US00PP30663P2

(12) United States Plant Patent
Cain

(10) Patent No.: US PP30,663 P2
(45) Date of Patent: Jul. 9, 2019

(54) GRAPEVINE PLANT NAMED 'IFG THIRTY-SEVEN'

(50) Latin Name: ***Vitis interspecific* hybrid**
Varietal Denomination: IFG Thirty-seven

(71) Applicant: David Cain, Bakersfield, CA (US)

(72) Inventor: David Cain, Bakersfield, CA (US)

(73) Assignee: International Fruit Genetics, LLC, Bakersfield, CA (US)

( * ) Notice: Subject to any disclaimer, the term of this patent is extended or adjusted under 35 U.S.C. 154(b) by 24 days.

(21) Appl. No.: 15/932,107

(22) Filed: Feb. 5, 2018

(51) Int. Cl.
*A01H 5/08* (2018.01)
*A01H 6/88* (2018.01)

(52) U.S. Cl.
USPC ..... Plt./205
CPC ..... *A01H 6/88* (2018.05); *A01H 5/08* (2013.01)

(58) Field of Classification Search
USPC ..... Plt./205
CPC ..... A01H 5/0812
See application file for complete search history.

(56) References Cited

PUBLICATIONS

U.S. Appl. No. 15/732,705, filed Dec. 13, 2017, Cain.

*Primary Examiner* — Kent L Bell

(57) ABSTRACT

This invention is a new and distinct grapevine variety denominated 'IFG Thirty-seven'. The new grapevine is characterized by producing naturally large seedless red berries having a broad ellipsoidal shape with a mild labrusca flavor. Fruits have medium firm texture and have excellent eating quality. Berries color readily even in hot climatic conditions and produce completely colored red berries. Vines are productive and can be pruned to short spurs. Berries are borne on large, loose but well filled clusters that do not require any additional thinning.

1 Drawing Sheet

Latin name of the genus and species claimed: *Vitis interspecific* hybrid.

Variety denomination: 'IFG Thirty-seven'.

BACKGROUND OF THE INVENTION

The new and distinct grapevine plant described and claimed herein originated from a hand pollinated cross of '01161-040-184' (unnamed *Vitis vinifera* selection from the IFG breeding program), and 'IFG Thirty-four' (U.S. Plant Pat. No. 30,325) hybridized in May 2008. The abortive seed traces were subsequently embryo cultured and the resulting 245 plants were planted in the field in April 2009. The present variety of grapevine was selected as a single plant in September 2011 and was first asexually propagated by hardwood cuttings in December 2011 near Delano, Kern County, Calif. These cuttings produced second generation plants that were planted during April 2012 near Delano, Kern County, Calif. and were observed for at least four years and found to be true-to-type.

BRIEF SUMMARY OF THE INVENTION

The new grapevine plant 'IFG Thirty-seven' is characterized by producing naturally large seedless red berries having a broad ellipsoidal shape with a mild labrusca flavor. Fruits have medium firm texture and have excellent eating quality. Berries color readily even in hot climatic conditions and produce completely colored red berries. Vines are productive and can be pruned to short spurs. Berries are borne on large, loose but well filled clusters that do not require any additional thinning. Berry size is naturally large but can be increased by applying gibberellic acid. The fruit stores well for up to eight weeks under commercial conditions.

'IFG Thirty-seven' can be distinguished from its maternal parent, the 01161-040-184, by having larger berry size, less firm flesh, having red instead of reddish black skin color and by having a mild fruity labrusca flavor as opposed to the neutral vinifera flavor of 01161-040-184.

The new grapevine differs from its pollen parent the 'IFG Thirty-four' by having brighter red rather than reddish black to black berry color; by having a broad ellipsoidal rather than round shape and by having much larger natural berry size and by having a larger cluster size and firmer berries.

'IFG Thirty-seven' is most similar to 'IFG Nineteen' (U.S. Plant Pat. No. 26,121) but differs by having a less vigorous growth habit, having smaller, more deeply lobed leaves, by having larger natural berries that have a mild labrusca flavor rather than a strong muscat/labrusca flavor of the 'IFG Nineteen'. 'IFG Thirty-seven' colors more easily than 'IFG Nineteen' does in hot climates.

'IFG Thirty-seven' is somewhat similar to its sibling the 'IFG Twenty-two' (U.S. Plant Pat. No. 26,541) but differs from 'IFG Twenty-two' by having a larger berry size, a broad ellipsoidal berry shape as opposed to a round to slightly elliptic shape of 'IFG Twenty-two', and having red rather than black berry color black color. It also has a milder flavor.

'IFG Thirty-seven' is also somewhat similar to its other sibling, 'IFG Thirty-six' (Plant patent application Ser. No. 15/932,108) filed concurrently with 'IFG Thirty-seven' (Plant patent application Ser. No. 15/932,107). It differs from the 'IFG Thirty-six' by having red rather than black berry color and by having a milder, more fruity flavor.

BRIEF DESCRIPTION OF THE DRAWING

The accompanying photographic drawing in FIG. 1 illustrates in full color 'IFG Thirty-seven', taken from a 4-year-old vine. The photograph was taken outdoors with indirect lighting. The colors are as nearly true as is reasonably possible in a color representation of this type.

The left side of the drawing has mature leaves.

A mature fruit cluster is represented in the center of the drawing along with a typical berry in cross section.

A young shoot can be seen on the right side of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2015 by The Royal Horticultural Society, London, England.

Throughout this specification, subjective description values conform to those set forth by the UPOV International Union for the Protection of New Varieties of Plants publication 'Grapevine *Vitis* L. Guidelines'.

The descriptive matter which follows pertains to 'IFG Thirty-seven' plants grown in the vicinity of Delano, Kern County, Calif. during 2016 and 2017, and is believed to apply to plants of the variety grown under similar conditions of soil and climate elsewhere:

VINE

General:

*Vigor*.—Vigorous.
*Density of foliage*.—Medium.
*Productivity*.—Productive, producing about 20.0 to 29.6 kg of fruit per vine.
*Root stock*.—Own root.
*Training method*.—Typically spur pruned leaving 2 bud spurs.

Trunk:

*Trunk diameter of* 4-*year-old vines at* 30 *cm above the soil line*.—About 4.2 cm.
*Shape*.—Medium stocky.
*Straps*.—Very long — continuous.
*Surface texture*.—Medium rough to shaggy texture.
*Inner bark color*.—The following colors were observed: Greyed-orange: 166A and 166B and 175A.
*Outer bark color*.—Greyed-brown: 201C.

SHOOTS

Young shoot:

*Form of tip*.—Fully opened.
*Distribution of anthocyanin coloration of tip*.—Absent.
*Intensity of anthocyanin coloration of tip*.—Absent.
*Density of prostrate hairs of tip*.—Sparse.
*Density of erect hairs on tip*.—Absent.
*Color*.—Yellow-green: 144A.

Woody shoot (mature canes):

*Internode length*.—Long: about 18.2 cm.
*Width at node*.—About 1.6 cm.
*Cross section*.—Circular.
*Surface*.—Smooth to slightly striate.
*Main color*.—The following colors were observed: Greyed-orange: 175A and 175B and 175C and 176A and 177A.
*Density of erect hairs on nodes*.—None.
*Density of erect hairs on internodes*.—None.
*Axillary shoot length at full bloom*.—Strong: approximately 23.9 cm.

Flowering shoot:

*Vigor during flowering*.—Strong.
*Attitude during flowering on shoots not tied*.—Semi-erect.
*Color*.—Dorsal side of internodes — Yellow-green: 146C.
*Color*.—Ventral side of internodes — Yellow-green: 146C, with Red-purple stripes: 59B.
*Color*.—Dorsal side of nodes — Yellow-green: 146C.
*Color*.—Ventral side of nodes — Yellow-green: 146C.
*Density of prostrate hairs on nodes*.—Very sparse.
*Density of erect hairs on nodes*.—None.
*Density of prostrate hairs on internode*.—None.
*Density of erect hairs on internode*.—None.
*Anthocyanin coloration of buds*.—Absent.

Tendrils:

*Distribution on the shoot* (*at full flowering*).—Discontinuous.
*Length of tendril*.—Long: about 37.8 cm.
*Thickness of tendril* 2 *cm from base*.—About 2.3 mm.
*Color*.—Yellow-green: 144C.
*Form*.—Bifurcated and trifurcated.
*Number of consecutive tendrils*.—2.

LEAVES

Young leaves:

*Color of upper surface of first four distal unfolded leaves*.—The following colors were observed: Yellow-green: 144A and Greyed-orange: 172A.
*Color of lower surface of young leaves*.—Yellow-green: 144A.
*Average intensity and color of anthocyanin coloration of six distal leaves prior to flowering*.—Absent or very weak: Greyed-purple: 183A.
*Density of prostrate hairs between veins* (*lower surface*).—Absent.
*Density of prostrate hairs on veins* (*lower surface*).—Very sparse.
*Density of erect hairs between veins* (*lower surface*).—Absent.
*Density of erect hairs on veins* (*lower surface*).—Very sparse.

Mature leaves (opposite first cluster):

*Average length*.—About 16.4 cm.
*Average width*.—About 20.4 cm.
*Mature leaf size*.—Large.
*Shape of blade*.—Wedge-shaped.
*Number of lobes*.—5.
*Blade venation*.—Palmate.
*Anthocyanin coloration of main veins on upper side of blade*.—Absent.
*Mature leaf profile*.—Undulate.

*Blistering surface of blade upper surface*.—Weak.
*Leaf blade tip*.—In the plane of the leaf.
*Leaf apex*.—Acute.
*Lear margin*.—Serrate.
*Undulation of margin*.—Slight.
*Undulation of blade between main and lateral veins*.—Absent.
*Shape of teeth*.—Mixture of both sides straight and both sides convex.
*Length of teeth*.—Long.
*Ratio length/width of teeth*.—Medium.
*Shape of upper lateral sinuses*.—Lobes strongly overlapping.
*Depth of upper lateral sinuses*.—Medium to somewhat deep.
*General shape petiole sinus*.—Half open.
*Shape of base of upper leaf sinuses*.—U-shaped.
*Tooth at petiole sinus*.—Absent.
*Density of prostrate hairs between veins on lower surface of blade*.—Absent to very sparse.
*Density of erect hairs between veins on lower surface of blade*.—Absent.
*Density of prostrate hairs on main veins on lower surface of blade*.—None or very sparse.
*Density of erect hairs on main veins on lower surface of blade*.—Sparse.
*Density of prostrate hairs on main veins on upper surface of blade*.—None or very sparse.
*Density of erect hairs on main veins on upper surface of blade*.—None.
*Autumn coloration of leaves*.—Greyed-yellow: 162A.

Upper surface:
*Color*.—Green: 137B.
*Anthocyanin coloration of main veins (lower surface)*.—Absent.
*Color of main veins*.—Yellow-green: 145B.
*Surface appearance*.—Dull.
*Blistering surface of blade*.—Weak.

Lower surface:
*Color*.—The following colors were observed: Yellow-green: 146B and 146C.
*Anthocyanin coloration of main veins (lower surface)*.—Absent.
*Color of main veins*.—Yellow-green: 145D.
*Glossiness*.—Weak.
*Surface texture*.—Smooth.
*Surface appearance*.—Dull.

Petiole:
*Length*.—About 15.3 cm.
*Diameter of petiole 2 cm from blade*.—3.3 mm.
*Petiole color*.—The following colors were observed: Yellow-green: 145C and Greyed-red: 182B.
*Length of petiole compared to middle vein*.—Slightly shorter.
*Density of prostrate hairs on petiole*.—Sparse.
*Density of erect hairs on petiole*.—None.

Buds:
*Bud fruitfulness*.—Basal: mostly fruitful.
*Position of first fruitful shoot on previous season cane*.—$1^{st}$ to $2^{nd}$ node.
*Dormant bud length*.—About 4.9 mm.
*Dormant bud width in the proximal/distal plane*.—About 5.0 mm.
*Dormant bud color*.—Greyed-orange: 166A.
*Time of bud burst*.—Midseason: About Mar. 18, 2017.

FLOWERS

General:
*Flower sex*.—Hermaphrodite.
*Length of single flower, unopened*.—About 3.6 mm.
*Width of single flower*.—Unopened: About 1.8 mm. Opened: About 6.9 mm.
*Stamen length*.—About 3.3 mm.
*Stamen count*.—5.
*Pollen color*.—Yellow: 10B.
*Pistil length*.—About 2.3 mm.
*Pistil color*.—Yellow-green: 144A.
*Length of first inflorescence*.—Medium: About 23.1 cm long by 11.0 cm wide.
*Position of first flowering and fruiting node*.—$4^{th}$ to $5^{th}$ node (current season growth).
*Number of inflorescence per flowering shoot*.—1.1 to 2: About 1.3.
*Time of bloom*.—Midseason as compared with similar varieties in the growing area of Delano, Calif.
*Date of full bloom*.—About May 10, 2017.

FRUIT

General:
*Ripening period*.—Early: approximately Jul. 30, 2016.
*Use*.—Fresh market.
*Keeping quality*.—Good, remains commercially acceptable when stored up to 8 weeks at 0° C. and high RH.
*Resistance to*.—Insects: Average typical of *Vitis vinifera* species. Diseases: Average typical of *Vitis vinifera* species.
*Refractometer test*.—Soluble solids: About 25.6 Brix.
*Brix/acid*.—About 49.2%.
*Titratable acidity*.—About 0.52.
*Juice ph*.—About 3.5.
*Juice color*.—Greyed-red: 182C.

Cluster:
*Mature cluster length (peduncle excluded)*.—About 25.6 cm.
*Mature cluster width*.—About 14.3 cm.
*Mature cluster weight*.—About 665 g.
*Bunch density*.—Medium: loosely distributed berries, pedicels visible, berries movable.
*Number of berries*.—About 106.
*Form*.—Conical.

Peduncle:
*Lignification of peduncle*.—Weak.
*Diameter of peduncle*.—About 4.5 mm.
*Length of peduncle*.—Long, approximately 6 to 7 cm.
*Color of peduncle*.—The following colors were observed: Yellow-green: 145B and 145C.

Berry:
*Uniformity of size*.—Uniform.
*Single berry weight*.—About 8.0 g natural.
*Shape*.—Broad ellipsoid.
*Seeds*.—Contains small rudimentary seed traces usually not noticeable.
*Cross section*.—Circular.
*Berry dimensions*.—Longitudinal axis: about 2.7 cm: Horizontal axis: about 2.2 cm.
*Pedicel length*.—About 9.1 mm.
*Pedicel width*.—About 1.8 mm.
*Pedicel color*.—Yellow-green: 145C.

*Berry firmness*.—Medium to firm.

*Particular flavor*.—Mild labrusca.

*Bloom* (*cuticular wax*).—Medium strong.

*Berry separation from pedicel*.—Average to slightly weak.

*Skin color* (*without bloom*).—The following colors were observed: Greyed-purple: N186C and N186D.

*Flesh color*.—Green-white: 157D.

Skin:

*Thickness*.—Medium.

*Skin toughness*.—Not notable when chewing.

*Reticulation*.—Absent.

*Tenacity*.—Tenacious to flesh.

What is claimed:

1. A new and distinct variety of grapevine plant as herein illustrated and described.

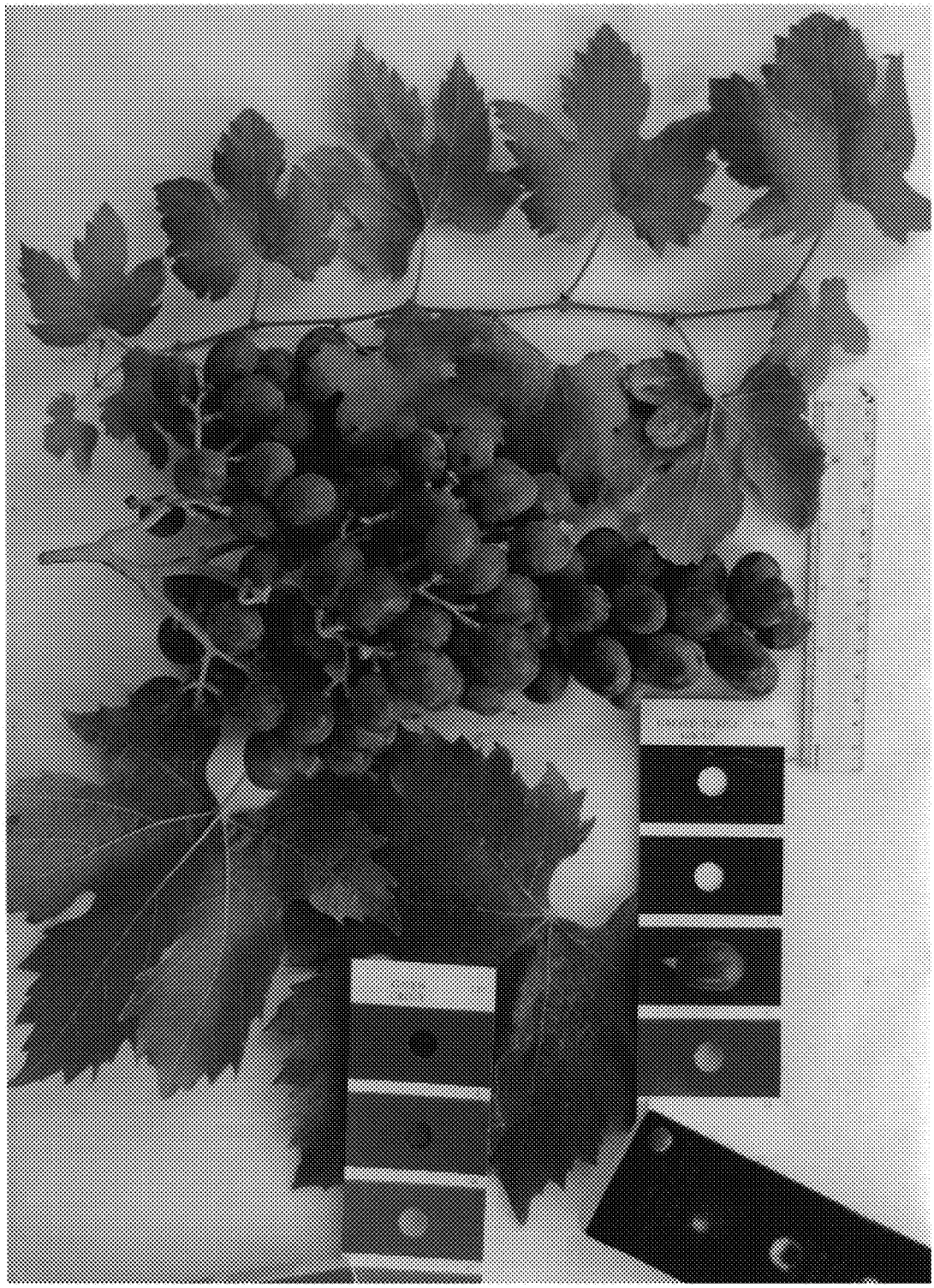

* * * * *